(12) United States Patent
Riester et al.

(10) Patent No.: US 10,610,570 B2
(45) Date of Patent: Apr. 7, 2020

(54) TREATING ROTATOR CUFF CONDITIONS

(71) Applicant: Mayo Foundation for Medical Education and Research, Rochester, MN (US)

(72) Inventors: Scott M. Riester, Rochester, MN (US); John W. Sperling, Rochester, MN (US); Andre J. van Wijnen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 131 days.

(21) Appl. No.: 15/321,767

(22) PCT Filed: Jul. 9, 2015

(86) PCT No.: PCT/US2015/039743
§ 371 (c)(1),
(2) Date: Dec. 23, 2016

(87) PCT Pub. No.: WO2016/007742
PCT Pub. Date: Jan. 14, 2016

(65) Prior Publication Data
US 2017/0128534 A1    May 11, 2017

Related U.S. Application Data

(60) Provisional application No. 62/022,516, filed on Jul. 9, 2014.

(51) Int. Cl.
| | | |
|---|---|---|
| *A61K 38/18* | (2006.01) | |
| *A61K 38/17* | (2006.01) | |
| *A61K 9/00* | (2006.01) | |
| *A61P 19/02* | (2006.01) | |
| *A61K 35/28* | (2015.01) | |
| *A61P 21/00* | (2006.01) | |

(52) U.S. Cl.
CPC ........ *A61K 38/1875* (2013.01); *A61K 9/0019* (2013.01); *A61K 35/28* (2013.01); *A61K 38/1709* (2013.01); *A61P 21/00* (2018.01)

(58) Field of Classification Search
None
See application file for complete search history.

(56) References Cited

U.S. PATENT DOCUMENTS

| | | | |
|---|---|---|---|
| 4,036,945 A | 7/1977 | Haber | |
| 4,331,647 A | 5/1982 | Goldenberg | |
| 5,939,388 A * | 8/1999 | Rosen | A61L 24/043 424/85.1 |
| 6,187,742 B1 * | 2/2001 | Wozney | A61K 38/1875 514/17.2 |
| 2003/0134308 A1 | 7/2003 | Clark et al. | |
| 2008/0027470 A1 | 1/2008 | Hart et al. | |
| 2010/0150885 A1 | 6/2010 | Tseng et al. | |
| 2011/0066242 A1 | 3/2011 | Lu et al. | |
| 2012/0328700 A1 | 12/2012 | Hill et al. | |
| 2013/0303620 A1 | 11/2013 | Burch et al. | |
| 2018/0200294 A1 | 7/2018 | Riester et al. | |

FOREIGN PATENT DOCUMENTS

| | | |
|---|---|---|
| JP | 2009-542681 | 12/2009 |
| JP | 2012-126720 | 7/2012 |
| WO | WO 1991/011465 | 8/1991 |
| WO | WO 2010/131038 | 11/2010 |

OTHER PUBLICATIONS

Barbas et al.., "Combinatorial immunoglobulin libraries on the surface of phage (Phabs): Rapid selection of antigen-specific fabs," *Methods* ., 2(2):119, Apr. 1991.
Baines et al., "Purification of Immunoglobulin G (IgG)", *Methods* ., 10:79-104, 1992.
Caring Medical Regenerative Medicine Clinics, "Prolotherapy for shoulder pain" (Oct. 18, 2011) [online] [retrieved on Sep. 15, 2016]. Retrieved from the Internet <URL: https://www.youtube.com/watch?v=eXI3cJQQKUA.
Caring Medical Regenerative Medicine Clinics, "Prolotherapy" (Apr. 12, 2015) [online] [retrieved on Sep. 15, 2016]. Retrieved from the Internet URL: http://vi'eb.archive.org/web/20150412171914/http://viww.caringmedical.com/prolofherapy/.
Carter et al., "Humanization of an anti-p185HER2 antibody for human cancer therapy," *Proc. Natl. Acad. Sci.USA*., 89(10):4285-4289, May, 15, 1992.
Dall'Acqua et al., "Antibody humanization by framework shuffling," *Methods*., 36:43-60, May 2005.
Damschroder et al., "Framework shuffling of antibodies to reduce immunogenicity and manipulate functional and biophysical properties," *Mol Immunol*., 44:3049-3060, 2007.
Deborah Gordon, "Rotator Cuff Injury and Regenerative Injection Therapy" Jan. 6, 2013, retrieved online on Jul. 20, 2017, Retrieved from the Internet, URL: http://www.drdeborahmd.com/rotator-cuff-injury-and-regenerative-injection-therapy.
Green et al., "Antigen-specific human monoclonal antibodies from mice engineered with human Ig heavy and light chain YACs," *Nature Genet*., 7:13-21, 1994.
Green et al., "Production of Polyclonal Antisera", *Immunochemical Protocols*., Humana Press, pp. 1-5, 1992.
Griffiths et al., "Isolation of high affinity human antibodies directly from large synthetic repertoires," *EMBO J*., 13(14):3245-3260, Jul. 15, 1994.
Gulotta et al., "Bone marrow-derived mesenchymal stem cells transduced with scleraxis improve rotator cuff healing in a rat model," *Am J Sports Med*., 39(6):1282-1289, Jun. 2011.

(Continued)

Primary Examiner — Emily A Cordas
(74) Attorney, Agent, or Firm — Fish & Richardson P.C.

(57) ABSTRACT

This document provides methods and materials related to treating rotator cuff conditions (e.g., rotator cuff tendonitis or rotator cuff injuries such as partial rotator cuff tears). For example, methods and materials for using BMP-5 polypeptides to treat rotator cuff conditions as well as methods and materials for using inhibitors of SIRT6, SIRT7, and/or HDAC10 polypeptide expression or activity to treat rotator cuff conditions are provided.

7 Claims, 3 Drawing Sheets

Specification includes a Sequence Listing.

(56) References Cited

OTHER PUBLICATIONS

He et al., "Thiomyristoyl peptides as cell-permeable Sirt6 inhibitors," *Org Biomol Chem.*, 12(38):7498-7502, Oct. 14, 2014.
Huse et al., "Generation of a large combinatorial library of the immunoglobulin repertoire in phage lambda," *Science.*, 246(4935):1275-1281, Dec. 8, 1989.
Hwang et al., "Use of human germline genes in a CDR homology-based approach to antibody humanization," *Methods.*, 36:35-42, May 2005.
International Preliminary Report on Patentability of the International Application No. PCT/US2015/039743, dated Jan. 10, 2017, 9 pages.
International Search Report and Written Opinion of the International Application No. PCT/US2015/39743, dated Dec. 8, 2015, 19 pages.
International Search Report and Written Opinion of the International Application No. PCT/US2016/42531, dated Oct. 13, 2016, 11 pages.
Jones et al., "Replacing the complementarity-determining regions in a human antibody with those from a mouse," *Nature.*, 321:522-525, May 29, 1986.
Kashmiri et al., "SDR grafting—a new approach to antibody humanization," *Methods.*, 36:25-34, May 2005.
Knappik et al., "Fully synthetic human combinatorial antibody libraries (HuCAL) based on modular consensus frameworks and CDRs randomized with trinucleotides," *J Mol Biol.*, 296:57-86, Feb. 11, 2000.
Kohler & Milstein, "Continuous cultures of fused cells secreting antibody of predefined specificity," *Nature.*, 256:495-497, Aug. 7, 1975.
Lazar et al., "A molecular immunology approach to antibody humanization and functional optimization," *Mol Immunol.*, 44(8):1986-1998, Mar. 2007.
Lonberg et al., "Antigen-specific human antibodies from mice comprising four distinct genetic modifications," *Nature.*, 368(6474):856-859, 1994.
Losman et al., "Baboon anti-idiotype antibodies mimic a carcinoembryonic antigen epitope," *Int J Cancer.*, 46:310-314, 1990.
Morikawa et al., "Contribution of oxidative stress to the degeneration of rotator cuff entheses," *J Shoulder Elbow Surg.*, 23(5):628-635, May 2014.
Nisonhoff et al., "Separation of univalent fragments from the bivalent rabbit antibody molecule by reduction of disulfide bonds," *Arch Biochem Biophys.*, 89(2):230-244, Aug. 1960.
Orlandi et al., "Cloning immunoglobulin variable domains for expression by the polymerase chain reaction," *Proc Natl Acad Sci USA.*, 86(10):3833-3837, May 1989.
Parenti et al., "Discovery of novel and selective SIRT6 inhibitors," *J Med Chem.*, 57(11):4796-4804, Jun. 12, 2014.
Porter, "The hydrolysis of rabbit y-globulin and antibodies with crystalline papain," *Biochem J.*, 73:119-126, 1959.
Radar et al., "A phage display approach for rapid antibody humanization: Designed combinatorial V gene libraries," *Proc Natl Acad Sci USA*, 95:8910-8915, Jul. 1998.
Riechmann et al., "Reshaping human antibodies for therapy," *Nature.*, 332(6162):323-327, Mar. 24, 1988.
Rosok et al., "A combinatorial library strategy for the rapid humanization of anticarcinoma BR96 Fab," *J Biol Chem.*, 271(37):22611-22618, 1996.
Sandhu., "Protein Engineering of Antibodies," *Crit Rev Biotech.*, 12(5):437-462, 1992.
Shibuya et al., "Palladium and platinum nanoparticles attenuate aging-like skin atrophy via antioxidant activity in mice," *PLoS One.*, 9(10):e109288, 9 pages, Oct. 15, 2014.
Simons et al., "Patient information: Rotator cuff tendinitis and tear (Beyond the Basics)" (Jul. 18, 2013) [online] [retrieved on Sep. 15, 2016]. Retrieved from the Internet <URL: http://Meb.archive.org/web/20130718152310/http://vvww.uptodate.com/contents/rotator-cufftendinitis-and-tear-beyond-the-basics?view=print> 26 pages.
Singer et al., "Optimal humanization of 1B4, an anti-CD18 murine monoclonal antibody, is achieved by correct choice of human V-region framework sequences," *J Immunol.*, 150(7):2844-2857, Apr. 1, 1993.
Taylor et al., "Human immunoglobulin transgenes undergo rearrangement, somatic mutation and class switching in mice that lack endogenous IgM," *Int Immunol.*, 6(4):579-597, Apr. 1994.
Verhoeyen et al., "Reshaping human antibodies: Grafting an antilysozyme activity," *Science.*, 239:1534-1536, 1988.
Wellmark, "Prolotherapy" May 26, 2015,Retrieved online Sep. 15, 2016 from the Internet, URL: http://www.wellmark.com/Provider/MedpoliciesAndAuthorizations/MedicalPolicies/policies/Prolotherapy.aspx.
Winter et al., "Making antibodies by phage display technology," *Ann Rev Immunol.*, 12: 433-455, Apr. 1994.
Summerton & Weller., "Morpholino Antisense Oligomers: Design, Preparation, and Properties," *Antisense Nucleic Acid Drug Development.*, 7:187-195, 1997.
U.S. Appl. No. 15/745,354, filed Jan. 16, 2018, Riester et al.
Ahn et al., "Differences of RNA expression in the tendon according to anatomic outcomes in rotator cuff repair," *Am J Sports Medicine.*, 45(13):2995-3003, Nov. 2017.
B.J.F. et al., "A systematic review of the histological and molecular changes in rotator cuff disease," *Bone Joint Research.*, 1(7):158-166, Jul. 23, 2012.
Chaudhury et al., "Gene expression profiles of changes underlying different-sied human rotator cuff tendon tears," *J Shoulder Elbow Surgery.*, 25(10):1561-1570, Apr. 27, 2016.
Chaudhury et al., "Lessons we can learn from gene expression patterns in rotator cuff tears and tendinopathies," *J Shoulder Elbow Surgery.*, 21(2):191-199, 2012.
International Preliminary Report on Patentability of the International Application No. PCT/US2016/42531, dated Jan. 16, 2018, 6 pages.
Kovacevic et al., "Biological augmentation of rotator cuff tendon repair," *Clin Orthop Relat Res.*, 466(3):622-633, Feb. 10, 2008.
Partial Supplementary European Search Report in International Application No. EP15818814.4, dated Feb. 26, 2018, 13 pages.
Cacchio et al., "Effectiveness of treatment of calcific tendinitis of the shoulder by disodium EDTA," *Arthritis Care & Research*, 61(1):84-91, Jan. 15, 2009.
Dean et al., "A systematic review of the histological and molecular changes in rotator cuff disease," Bone and Joint Research, 1(7):158-166, Jul. 2012.
Japanse Office action in Japanese Application No. 2017-500883 dated May 8, 2019, 47 pages, English translation.
Van der Sande et al., "Subacromial impingement syndrome: effectiveness of pharmaceutical interventions—nonsteroidal anti-inflammatory drugs, corticosteroid, or other injections: a systematic review," Archives of physical medicine and rehabilitation, 94(5):961-976, Dec. 12, 2012.

* cited by examiner

MHLTVFLLKGIVGFLWSCWVLVGYAKGGLGDNHVHSSFIYRRLRNHERREIQREILSILG
LPHRPRPFSPGKQASSAPLFMLDLYNAMTNEENPEESEYSVRASLAEETRGARKGYPAS
PNGYPRRIQLSRTTPLTTQSPPLASLHDTNFLNDADMVMSFVNLVERDKDFSHQRRHYK
EFRFDLTQIPHGEAVTAAEFRIYKDRSNNRFENETIKISIYQIIKEYTNRDADLFLLDTRKA
QALDVGWLVFDITVTSNHWVINPQNNLGLQLCAETGDGRSINVKSAGLVGRQGPQSKQ
PFMVAFFKASEVLLRSVRAANKRKNQNRNKSSSHQDSSRMSSVGGSSDVS (SEQ ID NO:1)

Figure 3

```
   1 actctttaga tctctcttga agagggctgg tatatttgtg cctgctggag gtggaattaa
  61 cagtaagaag gagaaaggga ttgaatggac ttacaggaag gatttcaagt aaattcaggg
 121 aaacacattt acttgaatag tacaacctag agtattattt tacactaaga cgacacaaaa
 181 gatgttaaag ttatcaccaa gctgccggac agatatatat tccaacacca aggtgcagat
 241 cagcatagat ctgtgattca gaaatcagga tttgttttgg aaagagctca agggttgaga
 301 agaactcaaa agcaagtgaa gattactttg ggaactacag tttatcagaa gatcaacttt
 361 tgctaattca aataccaaag gcctgattat cataaattca tataggaatg cataggtcat
 421 ctgatcaaat aatattagcc gtcttctgct acatcaatgc agcaaaaact cttaacaact
 481 gtggataatt ggaaatctga gtttcagctt tcttagaaat aactactctt gacatattcc
 541 aaaatattta aaataggaca ggaaatcgg tgaggatgtt gtgctcagaa atgtcactgt
 601 catgaaaaat aggtaaattt gttttttcag ctactgggaa actgtacctc ctagaaccttt
 661 aggtttttt ttttttaag aggacaagaa ggactaaaaa tatcaacttt tgcttttgga
 721 caaaaatgca tctgactgta tttttactta agggtattgt gggtttcctc tggagctgct
 781 gggttctagt gggttatgca aaaggaggtt tgggagacaa tcatgttcac tccagtttta
 841 tttatagaag actacggaac cacgaaagac gggaaataca aagggaaatt ctctctatct
 901 tgggtttgcc tcacagaccc agccattttt cacctggaaa acaagcgtcc tctgcacctc
 961 tctttatgct ggatctctac aatgccatga ccaatgaaga aaatcctgaa gagtcggagt
1021 actcagtaag ggcatccttg gcagaagaga ccagagggc aagaaaggga tacccagcct
1081 ctcccaatgg gtatcctcgt cgcatacagt tatctcggac gactcctctg accacccaga
1141 gtcctcctct agccagcctc catgatacca actttctgaa tgatgctgac atggtcatga
1201 gctttgtcaa cttagttgaa agagacaagg attttttctca ccagcgaagg cattacaaag
1261 aatttcgatt tgatcttacc caaattcctc atggagaggc agtgacagca gctgaattcc
1321 ggatatacaa ggaccggagc aacaaccgat tgaaaatga acaattaag attagcatat
1381 atcaaatcat caaggaatac acaaataggg atgcagatct gttcttgtta gacacaagaa
1441 aggcccaagc tttagatgtg ggttggcttg tctttgatat cactgtgacc agcaatcatt
1501 gggtgattaa tccccagaat aatttgggct tacagctctg tgcagaaaca ggggatggac
1561 gcagtatcaa cgtaaaatct gctggtcttg tgggaagaca gggacctcag tcaaaacaac
1621 cattcatggt ggccttcttc aaggcgagtg aggtacttct tcgatccgtg agagcagcca
1681 acaaacgaaa aaatcaaaac cgcaataaat ccagctctca tcaggactcc tccagaatgt
1741 ccagtgttgg aggttcatct gatgtttcct gaccacgtac caaagccttg ttgtgctcca
1801 accaaattaa atgccatctc tgttctgtac tttgatgaca   (SEQ ID NO:2)
```

TREATING ROTATOR CUFF CONDITIONS

CROSS REFERENCE TO RELATED APPLICATIONS

This application is a National Stage application under 35 U.S.C. § 371 of International Application No. PCT/US2015/039743, having an International Filing Date of Jul. 9, 2015, which claims the benefit of U.S. Provisional Ser. No. 62/022,516 filed Jul. 9, 2014. This disclosure of the prior application is considered part of (and is incorporated by reference in) the disclosure of this application.

BACKGROUND

1. Technical Field

This document provides methods and materials related to treating rotator cuff conditions (e.g., rotator cuff tendonitis or rotator cuff injuries such as partial or complete rotator cuff tears). For example, this document provides methods and materials for using BMP-5 polypeptides and/or inhibitors of SIRT6, SIRT7, and/or HDAC10 polypeptide expression or activity to treat rotator cuff conditions.

2. Background Information

The rotator cuff is a group of muscles and tendons that surround the shoulder joint, keeping the head of your upper arm bone firmly within the shallow socket of the shoulder. A rotator cuff injury can cause pain as well as loss of shoulder function.

SUMMARY

This document provides methods and materials related to treating rotator cuff conditions (e.g., rotator cuff tendonitis or rotator cuff injuries such as partial or complete rotator cuff tears). For example, this document provides methods and materials for using BMP-5 polypeptides to treat rotator cuff conditions. In some cases, a composition that includes BMP-5 polypeptides and/or cells (e.g., stem cells) designed to express BMP-5 polypeptides can be administered to (e.g., injected into) the rotator cuff region of a mammal suffering from a rotator cuff condition. In some cases, a composition that includes BMP-5 polypeptides and/or cells (e.g., stem cells) designed to express BMP-5 polypeptides can be introduced at the time of a surgical repair. In such cases, the administered (e.g., injected) composition can reduce or reverse tendon degeneration, enhance healing, and/or increase tendon strength.

This document also provides methods and materials for using inhibitors of SIRT6, SIRT7, and/or HDAC10 polypeptide expression or activity to treat rotator cuff conditions. In some cases, a composition that includes one or more inhibitors of SIRT6, SIRT7, and/or HDAC10 polypeptide expression or activity can be administered to (e.g., injected into) the rotator cuff region of a mammal suffering from a rotator cuff condition. In such cases, the administered (e.g., injected) composition can reduce or reverse tendon degeneration, enhance healing, and/or increase tendon strength. In some cases, inhibitors of SIRT6, SIRT7, and/or HDAC10 polypeptide expression or activity can be used alone or in conjunction with BMP-5 polypeptides to treat a rotator cuff condition. For example, an inhibitor of HDAC10 expression can be combined with a BMP-5 polypeptide to form a composition that is used to treat a mammal suffering from a rotator cuff condition.

In general, one aspect of this document features a method for treating a mammal having a rotator cuff condition. The method comprises, or consists essentially of, injecting a composition comprising a BMP-5 polypeptide into a rotator cuff region of the mammal, wherein injection of the composition reduces or reverses tendon degeneration, enhances tendon healing, or increases tendon strength. The mammal can be a human. The rotator cuff condition can be a rotator cuff condition wherein a rotator cuff tendon is partially torn. The rotator cuff condition can be a rotator cuff condition wherein a rotator cuff tendon is ruptured. The rotator cuff condition can be rotator cuff tendonitis. The injection can be an intra-articular injection into a joint space. The injection can be an injection into a subacromial space. The injection can be a direct injection into a damaged tendon. The BMP-5 polypeptide can be a human BMP-5 polypeptide. The BMP-5 polypeptide can comprise the amino acid sequence set forth in SEQ ID NO:1.

In another aspect, this document features a method for treating a mammal having a rotator cuff condition. The method comprises, or consists essentially of, administering a composition into a rotator cuff region of the mammal, wherein composition comprises cells comprising an exogenous nucleic acid encoding a BMP-5 polypeptide, wherein the cells express the BMP-5 polypeptide, and wherein administration of the composition reduces or reverses tendon degeneration, enhances tendon healing, or increases tendon strength. The mammal can be a human. The rotator cuff condition can be a rotator cuff condition wherein a rotator cuff tendon is partially torn. The rotator cuff condition can be a rotator cuff condition wherein a rotator cuff tendon is ruptured. The rotator cuff condition can be rotator cuff tendonitis. The administration can be an intra-articular injection into a joint space. The administration can be an injection into a subacromial space. The administration can be a direct injection into a damaged tendon. The BMP-5 polypeptide can be a human BMP-5 polypeptide. The BMP-5 polypeptide can comprise the amino acid sequence set forth in SEQ ID NO:1.

In another aspect, this document features a method for treating a mammal having a rotator cuff condition. The method comprises, or consists essentially of, administering a composition to a rotator cuff region of the mammal, wherein the composition comprises an inhibitor of SIRT6, SIRT7, or HDAC10 polypeptide expression or activity, wherein administration of the composition reduces or reverses tendon degeneration, enhances tendon healing, or increases tendon strength. The mammal can be a human. The rotator cuff condition can be a rotator cuff condition wherein a rotator cuff tendon is partially torn. The rotator cuff condition can be a rotator cuff condition wherein a rotator cuff tendon is ruptured. The rotator cuff condition can be rotator cuff tendonitis. The administration can be an intra-articular injection into a joint space. The administration can be an injection into a subacromial space. The administration can be a direct injection into a damaged tendon. The composition can comprise an inhibitor of SIRT6 polypeptide expression or activity. The composition can comprise an inhibitor of SIRT7 polypeptide expression or activity. The composition can comprise an inhibitor of HDAC10 polypeptide expression or activity (e.g., CUDC-907, pracinostat, abexinostat, or quisinostat). The composition can further comprise a BMP-5 polypeptide. The composition can further comprise cells comprising an exogenous nucleic acid encoding a BMP-5 polypeptide, wherein the cells express the BMP-5 polypeptide.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 3 is a nucleotide sequence (SEQ ID NO:2) listing of a nucleic acid that encodes a BMP-5 polypeptide.

DETAILED DESCRIPTION

This document provides methods and materials related to using BMP-5 polypeptides, cells expressing BMP-5 polypeptides, inhibitors of SIRT6 polypeptide expression or activity, inhibitors of SIRT7 polypeptide expression or activity, inhibitors of HDAC10 polypeptide expression or activity, or combinations thereof to treat rotator cuff conditions. For example, a composition that includes BMP-5 polypeptides and/or cells (e.g., stem cells) designed to express BMP-5 polypeptides can be administered to (e.g., injected into) the rotator cuff region of a mammal suffering from a rotator cuff condition. In such cases, the administered (e.g., injected) composition can reduce or reverse tendon degeneration, enhance healing, and/or increase tendon strength. Any appropriate rotator cuff condition can be treated as described herein. For example, rotator cuff tendonitis or rotator cuff injuries such as partial rotator cuff tears or rotator cuff ruptures can be treated as described herein. In addition, any appropriate mammal can be treated as described herein. For example, humans, monkeys, dogs, horses, sheep, pigs, goats, rabbits, rats or mice can be treated as described herein.

In some cases, a composition that includes BMP-5 polypeptides can be used to treat rotator cuff conditions. An example of a BMP-5 polypeptide that can be used as described herein includes, without limitation, a human BMP-5 polypeptide having the amino acid sequence set forth in SEQ ID NO:1. As described herein, a composition that includes a human BMP-5 polypeptide can be administered to a human having a rotator cuff condition under conditions wherein the composition reduces or reverses tendon degeneration, enhances healing, and/or increases tendon strength.

In some cases, a composition that includes one or more inhibitors of SIRT6, SIRT7, and/or HDAC10 polypeptide expression or activity can be used to treat rotator cuff conditions. Examples of inhibitors of SIRT6 polypeptide expression or activity include, without limitation, anti-SIRT6 antibodies, siRNA molecules against SIRT6, microRNAs targeting SIRT6, and constructs designed to edit genomic DNA to reduce expression of SIRT6 (e.g., CRISPR based strategies). Additional examples of inhibitors of SIRT6 polypeptide expression or activity include, without limitation, those inhibitors described elsewhere (see, e.g., Parenti et al., *J. Med. Chem.*, 57(11):4796-804 (2014) and He et al., *Org. Biomol. Chem.*, 12(38):7498-502 (2014)). In some cases, an inhibitor of SIRT6 polypeptide activity can have the following structure:

In some cases, commercial kits can be used to identify SIRT6 inhibitors. For example, the SIRT6 Inhibitor Screening Kit available from BioVision Inc. (Cat. No. K323-100) can be used to identify SIRT6 inhibitors.

Examples of inhibitors of SIRT7 polypeptide expression or activity include, without limitation, anti-SIRT7 antibodies, siRNA molecules against SIRT7, microRNAs targeting SIRT7, and constructs designed to edit genomic DNA to reduce expression of SIRT7 (e.g., CRISPR based strategies).

Examples of inhibitors of HDAC10 polypeptide expression or activity include, without limitation, anti-HDAC10 antibodies, siRNA molecules against HDAC10, microRNAs targeting HDAC10, constructs designed to edit genomic DNA to reduce expression of HDAC10 (e.g., CRISPR based strategies), CUDC-907, pracinostat (also known as SB939; (E)-3-(2-Butyl-1-(2-(diethylamino)ethyl)-1H-benzo[d]imidazol-5-yl)-N-hydroxyacrylamide), abexinostat (also known as PCI-24781; 3-[(Dimethylamino)methyl]-N-{2-[4-(hydroxycarbamoyl)phenoxy]ethyl}-1-benzofuran-2-carboxamide), quisinostat (N-Hydroxy-2-[4-({[(1-methyl-1H-indol-3-yl)methyl]amino}methyl)-1-piperidinyl]-5-pyrimidinecarboxamide), pracinostat (SB939), CUDC-101, CUDC-907, PCI-34051, and N-hydroxy-4-(2-((2-hydroxyethyl)(phenyl)amino)-2-oxoethyl)benzamide (CAS 1429651-50-2).

As described herein, a composition that includes one or more inhibitors of SIRT6, SIRT7, and/or HDAC10 polypeptide expression or activity can be administered to a human having a rotator cuff condition under conditions wherein the composition reduces or reverses tendon degeneration, enhances healing, and/or increases tendon strength.

The term "antibody" as used herein refers to intact antibodies as well as antibody fragments that retain some ability to bind an epitope. Such fragments include, without limitation, Fab, F(ab')$_2$, and Fv antibody fragments. The term "epitope" refers to an antigenic determinant on an antigen to which the paratope of an antibody binds. Epitopic determinants usually consist of chemically active surface groupings of molecules (e.g., amino acid or sugar residues) and usually have specific three dimensional structural characteristics as well as specific charge characteristics.

The antibodies provided herein can be any antibody (e.g., a monoclonal antibody) having binding affinity (e.g., specific binding affinity) for a SIRT6, SIRT7, or HDAC10 polypeptide. For example, an anti-SIRT6 antibody preparation or an anti-SIRT7 antibody preparation provided herein can be a preparation of Fab fragments having the ability to bind to SIRT6 (e.g., human SIRT6) or SIRT7 (e.g., a human SIRT7). Any appropriate method can be used to produce Fab fragments from intact antibodies. For example, standard papain digestion methods can be used to make a Fab antibody preparation.

Antibodies provided herein can be prepared using any appropriate method. For example, a sample containing a human SIRT6 polypeptide can be used as an immunogen to elicit an immune response in an animal such that specific antibodies are produced. The immunogen used to immunize an animal can be chemically synthesized or derived from translated cDNA. In some cases, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

The preparation of polyclonal antibodies is well known to those skilled in the art. See, e.g., Green et al., Production of Polyclonal Antisera, in IMMUNOCHEMICAL PROTOCOLS (Manson, ed.), pages 1 5 (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992). In addition, those of skill in the art will know of various techniques common in the immunology arts for purification and concentration of polyclonal antibodies, as well as monoclonal antibodies (Coligan, et al., Unit 9, Current Protocols in Immunology, Wiley Interscience, 1994).

The preparation of monoclonal antibodies also is well known to those skilled in the art. See, e.g., Kohler & Milstein, Nature 256:495 (1975); Coligan et al., sections 2.5.1 2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with PROTEIN A SEPHAROSE®, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS IN MOLECULAR BIOLOGY, VOL. 10, pages 79 104 (Humana Press 1992).

In addition, methods of in vitro and in vivo multiplication of monoclonal antibodies are well known to those skilled in the art. Multiplication in vitro can be carried out in suitable culture media such as Dulbecco's Modified Eagle Medium or RPMI 1640 medium, optionally replenished by mammalian serum such as fetal calf serum, or trace elements and growth sustaining supplements such as normal mouse peritoneal exudate cells, spleen cells, and bone marrow macrophages. Production in vitro provides relatively pure antibody preparations and allows scale up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells (e.g., osyngeneic mice) to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

In some cases, the antibodies provided herein can be made using non-human primates. General techniques for raising therapeutically useful antibodies in baboons can be found, for example, in Goldenberg et al., International Patent Publication WO 91/11465 (1991) and Losman et al., Int. J. Cancer, 46:310 (1990).

In some cases, the antibodies can be humanized monoclonal antibodies. Humanized monoclonal antibodies can be produced by transferring mouse complementarity determining regions (CDRs) from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions when treating humans. General techniques for cloning murine immunoglobulin variable domains are described, for example, by Orlandi et al., Proc. Nat'l. Acad. Sci. USA 86:3833 (1989). Techniques for producing humanized monoclonal antibodies are described, for example, by Jones et al., Nature 321:522 (1986); Riechmann et al., Nature 332:323 (1988); Verhoeyen et al., Science 239:1534 (1988); Carter et al., Proc. Nat'l. Acad. Sci. USA 89:4285 (1992); and Sandhu, Crit. Rev. Biotech. 12:437 (1992); Singer et al., J. Immunol. 150:2844 (1993). In some cases, humanization such as super humanization can be used as described elsewhere (Hwang et al., Methods, 36:35-42 (2005)). In some cases, SDR grafting (Kashmiri et al., Methods, 36:25-34 (2005)), human string content optimization (Lazar et al., Mol. Immunol., 44:1986-1998 (2007)), framework shuffling (Dall'Acqua et al., Methods, 36:43-60 (2005); and Damschroder et al., Mol. Immunol., 44:3049-3060 (2007)), and phage display approaches (Rosok et al., J. Biol. Chem., 271:22611-22618 (1996); Radar et al., Proc. Natl Acad. Sci. USA, 95:8910-8915 (1998); and Huse et al., Science, 246:1275-1281 (1989)) can be used to obtain anti-SIRT6, anti-SIRT7, or anti-HDAC10 antibody preparations. In some cases, fully human antibodies can be generated from recombinant human antibody library screening techniques as described elsewhere (Griffiths et al., EMBO J., 13:3245-3260 (1994); and Knappik et al., J. Mol. Biol., 296:57-86 (2000)).

Antibodies provided herein can be derived from human antibody fragments isolated from a combinatorial immunoglobulin library. See, for example, Barbas et al., METHODS: A COMPANION TO METHODS IN ENZYMOLOGY, VOL. 2, page 119 (1991) and Winter et al., Ann. Rev. Immunol. 12: 433 (1994). Cloning and expression vectors that are useful for producing a human immunoglobulin phage library can be obtained, for example, from STRATAGENE Cloning Systems (La Jolla, Calif.).

In addition, antibodies provided herein can be derived from a human monoclonal antibody. Such antibodies can be obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody secreting hybridomas. Methods for obtaining human antibodies from transgenic mice are described by Green et al. (*Nature Genet.*, 7:13 (1994)), Lonberg et al. (*Nature*, 368:856 (1994)), and Taylor et al. (*Int. Immunol.*, 6:579 (1994)).

Antibody fragments can be prepared by proteolytic hydrolysis of an intact antibody or by the expression of a nucleic acid encoding the fragment. Antibody fragments can be obtained by pepsin or papain digestion of intact antibodies by conventional methods. For example, Fab fragments can be produced by enzymatic cleavage of antibodies with papain. In some cases, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. In some cases, an enzymatic cleavage using pepsin can be used to produce two monovalent Fab' fragments and an Fc fragment directly. These methods are described, for example, by Goldenberg (U.S. Pat. Nos. 4,036,945 and 4,331,647). See also Nisonhoff et al., *Arch. Biochem. Biophys.* 89:230 (1960); Porter, *Biochem. J.* 73:119 (1959); Edelman et al., METHODS IN ENZYMOLOGY, VOL. 1, page 422 (Academic Press 1967); and Coligan et al. at sections 2.8.1 2.8.10 and 2.10.1 2.10.4.

Other methods of cleaving antibodies, such as separation of heavy chains to form monovalent light heavy chain fragments, further cleavage of fragments, or other enzymatic, chemical, or genetic techniques may also be used provided the fragments retain some ability to bind (e.g., selectively bind) its epitope.

The antibodies provided herein can be substantially pure. The term "substantially pure" as used herein with reference to an antibody means the antibody is substantially free of other polypeptides, lipids, carbohydrates, and nucleic acid with which it is naturally associated. Thus, a substantially pure antibody is any antibody that is removed from its natural environment and is at least 60 percent pure. A substantially pure antibody can be at least about 65, 70, 75, 80, 85, 90, 95, or 99 percent pure.

In some cases, a composition that includes one or more inhibitors of a BMP-5 polypeptide inhibitor can be used to treat rotator cuff conditions. Examples of BMP-5 polypeptide inhibitors include, without limitation, a Noggin polypeptide, chordin, gremlin, glycosaminoglycans (GAGs), and GAG modifying enzymes. Examples of inhibitors of a BMP-5 polypeptide inhibitor include, without limitation, anti-Noggin, anti-chordin, and anti-gremlin antibodies, and siRNA molecules against Noggin, chordin, and gremlin. Administration of such inhibitors of a BMP-5 polypeptide inhibitor can reduce or block the activity of a BMP-5 polypeptide inhibitor to enhance BMP-5 signaling in injured or degenerative rotator cuff tendons.

In some cases, a composition that includes cells expressing a BMP-5 polypeptide can be used to treat rotator cuff conditions. For example, cells (e.g., stem cells) can be transfected to include exogenous nucleic acid (e.g., an expression vector) that encodes a BMP-5 polypeptide. In such cases, the cells can express the BMP-5 polypeptides. Examples of cells that can be designed to express BMP-5 polypeptides and used to treat rotator cuff conditions include, without limitation, stem cells (e.g., adipose derived stem cells, bone marrow derived stem cells, induced pluripotent stem cells, and primary mesenchymal cells), osteoblasts, and osteoblastic cells, cells within bone or bone fragments cultured ex vivo, and cell lines capable of producing recombinant polypeptides (e.g. CHO, COS, and Hela cells). In some cases, the cells can be cells obtained from the mammal (e.g., human) that is being treated. For example, stem cells can be obtained from a patient, designed to express human BMP-5 polypeptides, and administered to that same patient. Examples of vectors that can be used to direct the expression of BMP-5 within cells include, without limitation, plasmids, synthetic mRNAs, and viral vectors (e.g., AAV, foamy virus, sendai virus, lentivirus, measles virus, or adenovirus vectors).

A composition provided herein (e.g., a composition containing a BMP-5 polypeptide or a cell designed to express a BMP-5 polypeptide) can be administered to a rotator cuff region of a mammal by intra-articular injection into the joint space, injection into the subacromial space, direct injection into damaged tendons, delivery as a topical at the time of surgical repair that could include delivery to the tendon itself, delivery to the bone tendon interface, or delivery directly into the joint space. In some cases, a composition provided herein (e.g., a composition containing a BMP-5 polypeptide or a cell designed to express a BMP-5 polypeptide) can be administered to a rotator cuff region of a mammal using a suture placed into the joint, adjacent to the tendon, or at the bone tendon interface.

In some cases, a composition provided herein (e.g., a composition containing a BMP-5 polypeptide or a cell designed to express a BMP-5 polypeptide) can lack a tissue scaffold (e.g., a biodegradable nanofiber scaffold or a collagen scaffold). For example, a liquid composition without a tissue scaffold structure can be designed to include a BMP-5 polypeptide or a cell designed to express a BMP-5 polypeptide and can be administered to (e.g., injected into) a mammal to treat a rotator cuff condition.

In some cases, the methods and materials provided herein (e.g., a composition containing a BMP-5 polypeptide or a cell designed to express a BMP-5 polypeptide) can be used to treat tendonitis or a tendon disorder such as an Achilles tendon disorder, a patellar tendon disorder, a quadriceps tendon disorder, or an epicondylitis.

The invention will be further described in the following examples, which do not limit the scope of the invention described in the claims.

EXAMPLES

Example 1—Assessment of Damaged/Ruptured Rotator Cuff Tendons

High throughput RNA-sequencing of intact and ruptured rotator cuff tendons was performed. The sequencing analysis initially identified the BMP receptor, ACVR1C, as being highly up-regulated in intact tendons versus damaged/ruptured rotator cuff tendons (Table 1).

TABLE 1

Expression of BMP receptors in rotator cuff tendon.

| Gene | Fold Change Intact vs Diseased Tendon |
|---|---|
| ACVR1 | 3.06 |
| ACVR1B | 4.41 |
| ACVR1C | 52.41 |
| ACVR2A | 4.15 |

TABLE 1-continued

Expression of BMP receptors in rotator cuff tendon.

| Gene | Fold Change Intact vs Diseased Tendon |
| --- | --- |
| ACVR2B | 2.27 |
| ACVRL1 | 0.76 |
| BMPR1A | 3.48 |
| BMPR1B | 1.57 |
| BMPR2 | 2.91 |

Once the ACVR1C receptor was identified, the ligands that bind to the ACVR1C receptor as well as downstream signaling molecules related to this receptor were evaluated. An evaluation of sequencing data revealed that BMP5 exhibited the greatest increase in expression amongst the possible ACVR1C receptor ligands, showing an 11.06 fold increase in intact rotator cuff tendon compared to diseased ruptured tendons (Table 2). A decrease in BMP signaling in damaged rotator cuff tendon also was confirmed by a reduction in the mRNA levels of the BMP specific SMAD proteins (SMAD1, SMAD5, and SMAD9), which are normally activated by the binding of BMPs to the ACVR1C receptor (Table 3).

TABLE 2

Expression of BMP in intact versus diseased rotator cuff tendon.

| Gene | Fold Change Intact vs Diseased Tendon |
| --- | --- |
| BMP1 | 0.34 |
| BMP2 | 1.54 |
| BMP2K | 1.69 |
| BMP4 | 2.72 |
| BMP5 | 11.06 |
| BMP6 | 3.17 |
| BMP7 | 0.59 |
| BMP8A | 1.09 |
| BMP8B | 2.49 |

TABLE 3

Expression of SMAD polypeptides that are activated via downstream signaling through ACVR1C.

| Gene | Fold Change Intact vs Diseased Tendon |
| --- | --- |
| SMAD1 | 6.17 |
| SMAD2 | 2.04 |
| SMAD3 | 2.26 |
| SMAD4 | 1.92 |
| SMAD5 | 3.25 |
| SMAD6 | 2.89 |
| SMAD7 | 2.92 |
| SMAD9 | 4.11 |

Figure 1:
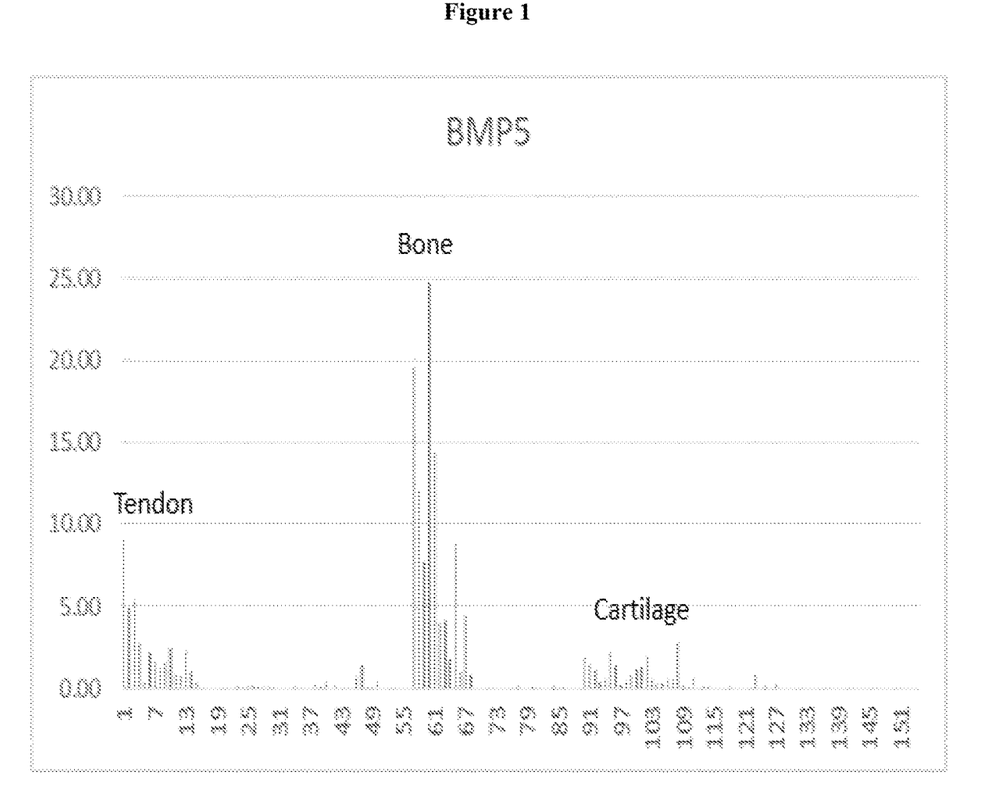
FIG. 1 is a graph plotting the level of BMP5 expression is various tissue types including bone, cartilage, muscle, tendon (supraspinatus, subscapularis, patellar tendon, posterior tibial tendon, and Achilles tendon), and ligament.
Figure 2:
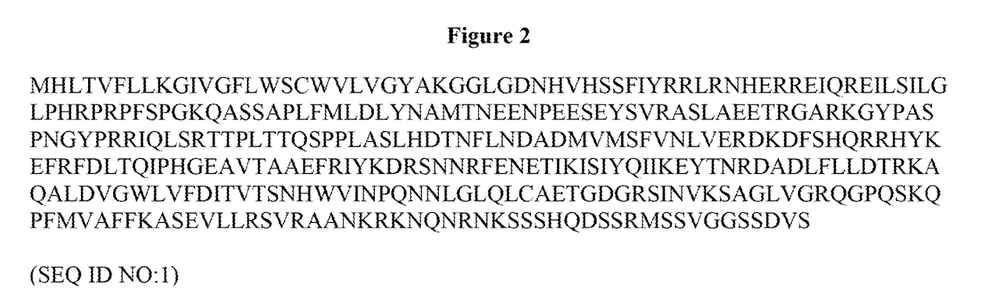
FIG. 2 is an amino acid sequence (SEQ ID NO:1) listing of a human BMP-5 polypeptide.

BMP5 expression also was examined across various tissue types including bone, cartilage, muscle, tendon, and ligament. BMP5 exhibited the highest levels of expression in bone, but it showed the second highest levels of expression in tendon (FIG. 1). These results suggest that BMP5 is involved in the maintenance of a normal tendon phenotype. These results also suggest that BMP5 polypeptides can be used therapeutically to treat degenerative rotator cuff disease, for example, as a prophylactic agent prior to rupture or as an adjunct to treat tendons that are undergoing repair (e.g., surgical repair).

RNA sequencing data also revealed a global down-regulation in gene expression in diseased rotator cuff tendon, which includes hundreds of regulatory transcription factors. SIRT6, SIRT7, HDAC10, RING1, and CARM1 are epigenetic regulators that promote gene silencing and were found to have elevated expression levels in degenerative tendon samples (Table 4).

TABLE 4

The expression of gene silencing epigenetic regulators in rotator cuff tendon.

| GeneID | Fold Change Diseased vs Intact Tendon |
| --- | --- |
| SIRT6 | 3.34 |
| HDAC10 | 2.48 |
| SIRT7 | 2.27 |
| RING1 | 2.26 |
| CARM1 | 2.06 |

These results suggest that SIRT6, SIRT7, HDAC10, RING1, and CARM1 are involved in the diseased rotator cuff tendon phenotype. These results also suggest that inhibitors of SIRT6, SIRT7, HDAC10, RING1, and CARM1 expression or activity can be used therapeutically to treat degenerative rotator cuff disease, for example, as a prophylactic agent prior to rupture or as an adjunct to treat tendons that are undergoing repair (e.g., surgical repair).

Example 2—Injecting BMP-5 Polypeptides to Treat Damaged/Ruptured Rotator Cuff Tendons BMP-5 polypeptides are synthesized at GMP-grade facilities using eukaryotic cells lines (e.g., CHO cells, HeLa cells, or adipose derived mesenchymal stem cells) to produce BMP-5. The BMP-5 is purified from cell extracts. 0.5 to 10 mg of BMP-5 polypeptide is formulated with 1 to 10 mL of 4 mM HCl or other soluble solution to obtain a liquid composition having a final concentration of about 0.5 to 5 mg/mL. This liquid composition is injected at a dose of 0.1 to 5 mg/mL directly into degenerative or surgically repaired tendons or into the joint space to deliver a total amount of BMP-5 in the range of 0.1 mg and 50 mg per administration.

Example 3—Injecting Cells Designed to Express BMP-5 Polypeptides to Treat Damaged/Ruptured Rotator Cuff Tendons A viral vector or other nucleic acid-based vector designed to express BMP-5 constitutively in a cell is introduced into stem cells or other somatic cell types. These modified cells are formulated with saline or other cell culture medium to obtain a liquid composition having a final concentration of about 100,000 to $20 \times 10^6$ cells/mL. This liquid composition is injected at a dose of about 100,000 to $20 \times 10^6$ cells/mL directly into a damaged tendon or a joint/subacromial space to deliver a total number of cells in the range of 100,000 and $20 \times 10^6$ per administration. BMP-5 expressing stem cells are injected with or without ultrasound guidance. In some cases, these techniques can be used to treat degenerative tendons at risk for rupture or to augment surgical repair of previously ruptured tendons.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having a rotator cuff condition, wherein said method comprises injecting a composition comprising (a) an inhibitor of histone deacetylase 10 (HDAC 10) polypeptide expression or activity and (b) a bone morphogenetic protein 5 (BMP-5) polypeptide into a rotator cuff region of said mammal, wherein injection of said composition reduces or reverses tendon degeneration, enhances tendon healing, or increases tendon strength.

2. The method of claim 1, wherein said mammal is a human.

3. The method of claim 1, wherein said rotator cuff condition is a rotator cuff condition wherein a rotator cuff tendon is partially torn or is ruptured.

4. The method of claim 3, wherein said injection is a direct injection into a damaged tendon.

5. The method of claim 3, wherein said BMP-5 polypeptide is a human BMP-5 polypeptide.

6. The method of claim 3, wherein said BMP-5 polypeptide comprises the amino acid sequence set forth in SEQ ID NO:1.

7. The method of claim 3, wherein said inhibitor is CUDC-907; (E)-3-(2-Butyl-1-(2-(diethylamino)ethyl)-1H-benzo[d]imidazol-5-yl)-N-hydroxyacrylamide; 3-[(Dimethylamino)methyl]-N-{2-[4-(hydroxycarbamoyl)phenoxy]ethyl}-1-benzofuran-2-carboxamide; N-Hydroxy-2-[4-({[(1-methyl-1H-indol-3-yl)methyl]amino}methyl)-1-piperidinyl]-5-pyrimidinecarboxamide; pracinostat; CUDC-101; PCI-34051; or N-hydroxy-4-(2-((2-hydroxyethyl)(phenyl)amino)-2-oxoethyl)benzamide.

* * * * *

SEQUENCE LISTING

<160> NUMBER OF SEQ ID NOS: 2

<210> SEQ ID NO 1
<211> LENGTH: 348
<212> TYPE: PRT
<213> ORGANISM: Homo sapiens

<400> SEQUENCE: 1

```
Met His Leu Thr Val Phe Leu Leu Lys Gly Ile Val Gly Phe Leu Trp
 1               5                  10                  15

Ser Cys Trp Val Leu Val Gly Tyr Ala Lys Gly Gly Leu Gly Asp Asn
                20                  25                  30

His Val His Ser Ser Phe Ile Tyr Arg Arg Leu Arg Asn His Glu Arg
            35                  40                  45

Arg Glu Ile Gln Arg Glu Ile Leu Ser Ile Leu Gly Leu Pro His Arg
        50                  55                  60

Pro Arg Pro Phe Ser Pro Gly Lys Gln Ala Ser Ser Ala Pro Leu Phe
65                  70                  75                  80

Met Leu Asp Leu Tyr Asn Ala Met Thr Asn Glu Glu Asn Pro Glu Glu
                85                  90                  95

Ser Glu Tyr Ser Val Arg Ala Ser Leu Ala Glu Glu Thr Arg Gly Ala
               100                 105                 110

Arg Lys Gly Tyr Pro Ala Ser Pro Asn Gly Tyr Pro Arg Arg Ile Gln
            115                 120                 125

Leu Ser Arg Thr Thr Pro Leu Thr Thr Gln Ser Pro Pro Leu Ala Ser
        130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
                165                 170                 175

Tyr Lys Glu Phe Arg Phe Asp Leu Thr Gln Ile Pro His Gly Glu Ala
            180                 185                 190

Val Thr Ala Ala Glu Phe Arg Ile Tyr Lys Asp Arg Ser Asn Asn Arg
        195                 200                 205

Phe Glu Asn Glu Thr Ile Lys Ile Ser Ile Tyr Gln Ile Ile Lys Glu
    210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
                245                 250                 255

Asn His Trp Val Ile Asn Pro Gln Asn Asn Leu Gly Leu Gln Leu Cys
            260                 265                 270

Ala Glu Thr Gly Asp Gly Arg Ser Ile Asn Val Lys Ser Ala Gly Leu
        275                 280                 285

Val Gly Arg Gln Gly Pro Gln Ser Lys Gln Pro Phe Met Val Ala Phe
    290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser Ser His Gln Asp Ser Ser
                325                 330                 335

Arg Met Ser Ser Val Gly Gly Ser Ser Asp Val Ser
            340                 345
```

-continued

```
<210> SEQ ID NO 2
<211> LENGTH: 1840
<212> TYPE: DNA
<213> ORGANISM: Homo sapiens

<400> SEQUENCE: 2
actctttaga tctctcttga agagggctgg tatatttgtg cctgctggag gtggaattaa      60
cagtaagaag gagaaaggga ttgaatggac ttacaggaag gatttcaagt aaattcaggg     120
aaacacattt acttgaatag tacaacctag agtattattt tacactaaga cgacacaaaa     180
gatgttaaag ttatcaccaa gctgccggac agatatatat tccaacacca aggtgcagat     240
cagcatagat ctgtgattca gaaatcagga tttgttttgg aaagagctca agggttgaga     300
agaactcaaa agcaagtgaa gattactttg ggaactacag tttatcagaa gatcaacttt     360
tgctaattca ataccaaag gcctgattat cataaattca tataggaatg cataggtcat      420
ctgatcaaat aatattagcc gtcttctgct acatcaatgc agcaaaaact cttaacaact     480
gtggataatt ggaaatctga gtttcagctt tcttagaaat aactactctt gacatattcc     540
aaaatattta aaataggaca ggaaaatcgg tgaggatgtt gtgctcagaa atgtcactgt     600
catgaaaaat aggtaaattt gttttttcag ctactgggaa actgtacctc ctagaacctt     660
aggttttttt ttttttttaag aggacaagaa ggactaaaaa tatcaacttt tgcttttgga     720
caaaaatgca tctgactgta tttttactta agggtattgt gggtttcctc tggagctgct     780
gggttctagt gggttatgca aaaggaggtt tgggagacaa tcatgttcac tccagtttta     840
tttatagaag actacggaac cacgaaagac gggaaataca aagggaaatt ctctctatct     900
tgggtttgcc tcacagaccc agaccatttt cacctggaaa acaagcgtcc tctgcacctc     960
tctttatgct ggatctctac aatgccatga ccaatgaaga aaatcctgaa gagtcggagt    1020
actcagtaag ggcatccttg gcagaagaga ccagaggggc aagaaaggga tacccagcct    1080
ctcccaatgg gtatcctcgt cgcatacagt tatctcggac gactcctctg accacccaga    1140
gtcctcctct agccagcctc catgatacca actttctgaa tgatgctgac atggtcatga    1200
gctttgtcaa cttagttgaa agagacaagg atttttctca ccagcgaagg cattacaaag    1260
aatttcgatt tgatcttacc caaattcctc atggagaggc agtgacagca gctgaattcc    1320
ggatatacaa ggaccggagc aacaaccgat ttgaaaatga aacaattaag attagcatat    1380
atcaaatcat caaggaatac acaaataggg atgcagatct gttcttgtta gacacaagaa    1440
aggcccaagc tttagatgtg ggttggcttg tctttgatat cactgtgacc agcaatcatt    1500
gggtgattaa tccccagaat aatttgggct tacagctctg tgcagaaaca ggggatggac    1560
gcagtatcaa cgtaaaatct gctggtcttg tgggaagaca gggacctcag tcaaaacaac    1620
cattcatggt ggccttcttc aaggcgagtg aggtacttct tcgatccgtg agagcagcca    1680
acaaacgaaa aaatcaaaac cgcaataaat ccagctctca tcaggactcc tccagaatgt    1740
ccagtgttgg aggttcatct gatgtttcct gaccacgtac caaagccttg ttgtgctcca    1800
accaaattaa atgccatctc tgttctgtac tttgatgaca                          1840
```

UNITED STATES PATENT AND TRADEMARK OFFICE
CERTIFICATE OF CORRECTION

PATENT NO. : 10,610,570 B2
APPLICATION NO. : 15/321767
DATED : April 7, 2020
INVENTOR(S) : Scott M. Riester, John W. Sperling and Andre J. van Wijnen It is certified that error appears in the above-identified patent and that said Letters Patent is hereby corrected as shown below:

In the Claims

Column 15, Line 1, Claim 4, delete "claim 3," and insert -- claim 1, --, therefor;

Column 15, Line 3, Claim 5, delete "claim 3," and insert -- claim 1, --, therefor;

Column 15, Line 5, Claim 6, delete "claim 3," and insert -- claim 1, --, therefor;

Column 15, Line 8, Claim 7, delete "claim 3," and insert -- claim 1, --, therefor.

Signed and Sealed this
Twenty-second Day of September, 2020

Andrei Iancu
*Director of the United States Patent and Trademark Office*